US00PP21837P2

(12) United States Plant Patent
Chaparro et al.

(10) Patent No.: US PP21,837 P2
(45) Date of Patent: Apr. 5, 2011

(54) PEACH TREE NAMED 'UFGLO'

(50) Latin Name: ***Prunus persica* (L.) Batsch**
Varietal Denomination: UFGlo

(75) Inventors: Jose Chaparro, Gainesville, FL (US); Wayne Sherman, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/655,658

(22) Filed: Jan. 5, 2010

(51) Int. Cl.
*A01H 5/00* (2006.01)

(52) U.S. Cl. ..... Plt./195
(58) Field of Classification Search ..... Plt./195
See application file for complete search history.

*Primary Examiner* — Annette H Para

(57) ABSTRACT

A new and distinct variety of peach tree, denominated 'UFGlo', characterized by a winter chilling requirement estimated at 400 chill units (cu). The tree is medium size, moderately vigorous, and semi-spreading in growth habit. It bears showy, pink flowers, and leaves with reniform glands. Trees of 'UFGlo' are self-fertile and regularly bear heavy annual crops of early season fruit that are medium size (125g) for its ripening season. Fruit are uniformly firm with non-melting white flesh. Fruit are nearly round, and uniform with substantially symmetrical shape, and have an attractive 70 to 80% red skin. The fruit of 'UFGlo' usually ripen 10 to 14 days before 'UFSharp' peach in mid-May at Gainesville, Fla.

1 Drawing Sheet

Figure 1:
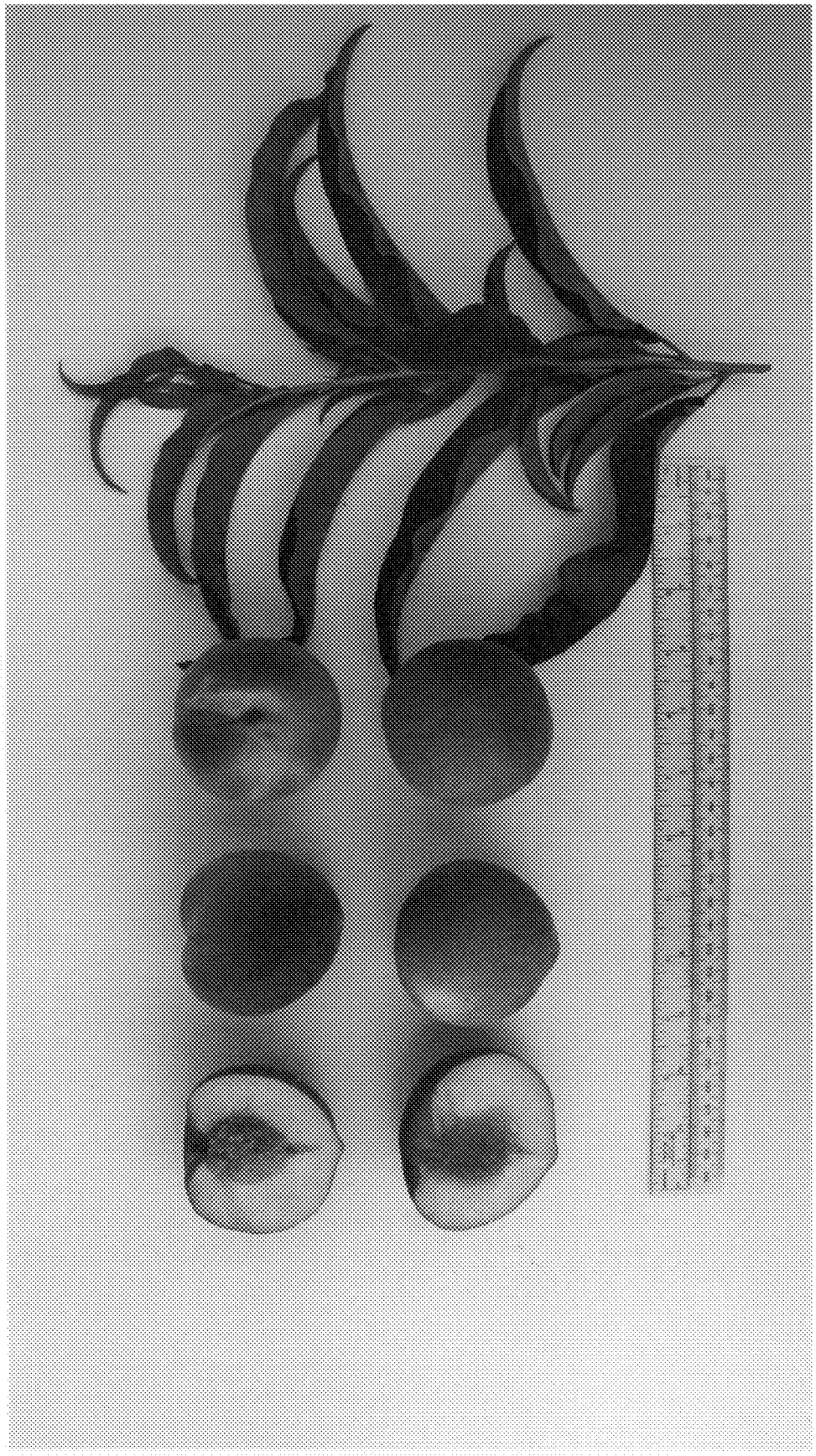

Genus and species: *Prunus persica* (L.) Batsch.
Variety denomination: 'UFGlo'.

BACKGROUND OF THE NEW PLANT

The invention relates to a new and distinct variety of peach tree, *Prunus persica* (L.) Batsch, named 'UFGlo'. 'UFGlo' is adapted to a subtropical (moderate chill) winter climate. 'UFGlo' produces highly colored, white and non-melting flesh fruit with good eating quality for fresh market in mid-May at Gainesville, Fla. Contrast is made to 'UFSharp' peach (U.S. patent application Ser. No. 12/592,576), a standard variety, for reliable description. 'UFGlo' is a promising candidate for commercial success in that it has attractive red skin, sweet fruit that ripen evenly.

'UFGlo' originated in a cultivated area in Gainesville, Fla. 'UFGlo' was selected in 2002 because it exhibited white, non-melting flesh, in a medium size fruit with a bright red skin. The original tree was grafted to 'Flordaguard' (unpatented) rootstock and was planted in Gainesville, Fla. in 2002. There are no known effects of this standard rootstock on this scion cultivar. 'UFGlo' has unique tree and fruit characteristics making it worthy for commercial fresh fruit production.

'UFGlo' has been subsequently asexually propagated by conventional bud-grafting onto 'Flordaguard' rootstocks in Gainesville, Fla. The present invention has been found to retain its distinctive characteristics through successive asexual propagations.

Plant Breeder's Rights for this cultivar have not been applied for. 'UFGlo' has not been made publicly available or sold more than one year prior to the filing of this application.

SUMMARY OF THE INVENTION

'UFGlo' is a new and distinct variety of peach tree which bears white, non-melting flesh fruit of good flavor, brix, and eating quality which ripens in mid-May at Gainesville, Fla. 'UFGlo' blooms in late February at Gainesville, Fla. and 10 to 14 days after 'UFSharp'. Thus, the chilling requirement for 'UFGlo' is estimated at 400 chill units.

'UFGlo' trees are vigorous, productive and without alternate bearing. 'UFGlo' trees attain in two years a height of two meters and a spread of one and half meters at Gainesville, Fla. Terminal growth of up to a half meter annually is common on mature 5-year-old trees of 'UFGlo' with normal pruning to a vase shape.

'UFGlo' fruit ripen the week following mid-May at Gainesville, Fla. or in about 80 days from full bloom, which is 10 to 15 days before 'UFSharp' ripening. The fruit of 'UFGlo' are uniformly medium size, averaging 130g when properly thinned to a full crop. However, 'UFGlo' fruit are more round than 'UFSharp' which has longer fruit. Ripe fruit of 'UFGlo' have averaged 80% red blush, but there is no red pigment in the flesh or at the pit. The flower anthers of 'UFGlo' are deep yellow, and leaf glands are reniform, common characteristics of many standard peach varieties. No buttons (parthenocarpy fruit) or split pits have been observed. The potential for commercial production of fresh fruit is high, due to its attractive red skin over a creamy white ground color, medium size fruit of good flavor, and good firmness with even ripening throughout the fruit.

The following are the most outstanding and distinguishing characteristics of this new cultivar when grown under normal horticultural practices in Florida.

1. Trees that bloom in late February at Gainesville, Fla. and 10 to 14 days after 'UFSharp'.
2. Fruit that ripens in mid-May in Gainesville, Fla., 10 to 14 days earlier than 'UFSharp'.
3. Fruit having high percentage red skin, white, non-melting, clingstone, and smooth textured flesh with good flavor, brix, firmness, and eating quality.

DESCRIPTION OF THE PHOTOGRAPHS

This new peach plant is illustrated by the accompanying photograph which shows a typical specimen of the fruit, leaf, and stem of the new variety as nearly true as it is reasonably possible to make in a color illustration of this type. The photograph was taken in May 2009.

FIG. 1 shows the shape and exterior coloration of 6 specimens of fruit of 'UFGlo' above a ruler in side view, stem end view, a blossom end view, a side view showing the suture and a fruit cut longitudinally to show with and without the pit.

DESCRIPTION OF THE NEW CULTIVAR

The following detailed description defines the characteristics of 'UFGlo'. The present botanical description is that of the variety grown at the University of Florida in Gainesville, Fla. in 2009 on 'Flordaguard' rootstock (second generation trees, 5 years old). The tree, flowers, and fruit of 'UFGlo' may vary in slight detail due to variations in soil type, cultural practices, and climatic condition. The colors (except those in common terms) are described from "The Pantone Book of Color", published by H. N. Abrams, Inc., N.Y. 1990.

DETAILED BOTANICAL DESCRIPTION

Classification:

*Botanical.*—*Prunus persica* (L.) Batsch.

*Common name.*—Peach.

*Parentage.*—Female parent: 'Fla. 97-47c' (unpatented). Male parent: Unknown, bulked pollen sample generated by combining pollen from three unselected, white-fleshed peaches heterozygous for non-melting flesh.

Tree:

*Form.*—Semi-spreading, but easily pruned to vase shape.

*Vigor.*—Moderately vigorous, and must be summer and winter pruned when grown to a vase shape to keep the tree open to get strong fruiting wood in the lower center; trees respond typically to irrigation and fertilization; tree growth of 4 to 6 feet in height and 3 to 5 feet in width occurs the first growing season in the field.

*Size.*—Trees are medium stature when trained to an open vase form.

*Trunk diameter* (*on 'Flordaguard' rootstock*).—8 cm diameter at a height of 30 cm at the end of 3 years growth at Gainesville.

*Trunk texture.*—Medium smooth, but changes to medium shaggy as tree ages.

*Trunk lenticels.*—Moderate number (6 to 12 per 4 square inches of surface area of trunk) and large (6 to 12 mm length perpendicular to the trunk), grey, Sponge (Pantone 16-1118) with the center being yellowish brown, Inca Gold (Pantone 17-1048).

*Bark color.*—Older bark gray, Chinchilla (Pantone 17-1109).

*Density.*—Light to medium in branching habit; pruning is required to open the tree center to promote sunlight entrance for enhancing fruit color and sugar.

*Hardiness.*—Hardy with respect to typical north central Florida winters.

*Bearer.*—Very productive annually without alternate bearing observed; trees are self fertile and must be fruit thinned to avoid limb breakage and obtain large fruit size; trees annually set several times the number of fruit for a desired crop load.

*Chilling requirement.*—Estimated endodormancy chilling requirement is 400 chill units based on time of bloom and leafing in relation to standard varieties.

Branches:

*Size.*—Strong growth of scaffold branches; fruiting branches are mostly large diameter (4 to 7 mm) and not overly twiggy, resulting in strong fruiting wood; thus, the tree growth and structure permits easier and faster winter pruning.

*Texture.*—Relatively smooth, medium size lenticels attaining size found on trunk and old scaffolds; roughness increases with age.

*Color.*—New wood is light green, Green Banana (Pantone 14-0434); Old wood is brown, Macaroon (Pantone 16-1323).

*Crotch angles.*—Angles are selected at 45 to near 90 degrees in first year of tree training; natural angles are within the normal range of standard varieties for a semi-spreading tree and similar to those of 'UFSharp'.

Leaves:

*Form.*—Lanceolate.

*Apex.*—Acute.

*Base.*—Cuneate.

*Margin.*—Serrulate, slightly undulate.

*Size.*—Medium; 15 to 17 cm length, including the petiole; 33 to 37 mm width (measurements made on vigorous upright shoots of summer growth).

*Thickness.*—Regular and average for commercial peach varieties.

*Surface.*—Upper, glabrous; Lower, medium large veins that are pinnately netted.

*Color.*—Lower surface is green, Peridot (Pantone 17-0336); upper surface is slightly darker green, Artichoke Green (Pantone 18-0125).

*Glands.*—Usually 4, medium size reniform glands on lower leaf blade, and petiole; leaf glands on young leaves are light green, Leek Green (Pantone 15-0628); size averages about 1 mm in length and 0.3 mm in width.

*Petiole.*—Length: Average 1 cm (0.8 to 1.2 cm). Diameter: 1.5 mm. Color: Light green, Oasis (Pantone 16-0540) on older leaves of summer. Shape: Grooved longitudinally.

*Stipules.*—Medium (equal to most commercial peach varieties), usually 2 per bud, and abscising just before leaf becomes full size in summer growth; color at full size is green, Olive Green (Pantone 17-0535), but tinged with anthocyanin before abscising.

*Arrangement.*—Alternate.

Flower buds:

*Hardiness.*—Hardy with respect to central Florida winters (16F minimum observed).

*Abundance.*—Very high due to visually shorter than average internode length; most buds set fruit in absence of spring frosts and show little evidence of bud drop.

*Size.*—Medium, average 6.0 mm length in mid winter.

*Form.*—Plump, conic and free.

*Surface.*—Pubescent scales.

*Color.*—Brown, Stucco (Pantone 16-1412) in late summer.

Flowers:

*Blooming period in north central Florida.*—7 to 10 days after 'UFSharp' peach — average 50% bloom February 15 to 20 most years at Gainesville, but occurring over a 7-10 day period; time and length of bloom are dependant on ambient temperature.

*Aroma.*—Not detectable.

*Flower density.*—Abundant, varying 1 to 3 per node, but usually 2.

*Type.*—Showy, location and seasonally variable within the range of commercial showy varieties; average flower diameter — 3.3 cm; average petal length, 14 mm; width — 13 mm.

*Texture.*—Smooth.

*Margins.*—Undulate and smooth.

*Color.*—Almond Blossom (Pantone 14-2307) at flower opening, and within the pink range of standard varieties.

*Flower parts.*—Stamens and pistil size, shape and color are within the range of standard commercial varieties; there are 5 sepals and petals; sepals average 5 mm length and 4 mm wide at attachment to calyx cup and rounded at the distal end; sepals are green, Cedar (Pantone 16-0526) on the interior and red, Garnet (Pantone 19-1655) on the exterior with a smooth pubescent margin; sepals are pubescent and petals are glabrous; pistils are usually 1 per flower and straight (without curls or curves) just prior to flower opening; pistil length (from tip of stigma to base of ovary) averages 16 mm; pistils are light green, Pale Star (Pantone 12-0626); flower pedicel is 2 to 4 mm length.

*Calyx cup.*—Medium large in the size range of commercial varieties; noticeably tough to cut in emasculations; diameter is 5 mm at the top, at the time of flower opening; exterior is red, Garnet (Pantone 19-1655) and interior of the cup base is light green, Frozen Dew (Pantone 13-0513).

*Stamen.*—Anthers are deep yellow, Apricot Orange (Pantone 17-1353), at flower opening; number of anthers varies from 33 to 41 and filament length is 10 to 14 mm; filaments are pink, Almond Blossom (Pantone 14-2307) at flower opening.

*Pollen.*—Abundant and yellow, Snapdragon (Pantone 13-0840).

*Fertility.*—Fully self fertile, and no cross pollination is required; fruit set is abundant.

Fruit:

*Maturity when described.*—Tree ripe, May 11, 2009 at Gainesville, Fla.

*Date of picking.*—First, May 11, 2009; Last, — May 18, 2009 at Gainesville, Fla.

*Size.*—Uniform, medium large (large size for early mid-season maturity at 130 to 150g); varies with fruit number per tree, soil type, climatic conditions and cultural practices. Average equatorial diameter: $2^{1/2}$ inches (63 mm). Average polar length (stem to distal end): 2⅝ inches (67 mm).

*Peduncle size and color.*—Length averages 4 mm; width is approximately 3 mm; color is green, Cedar (Pantone 16-0526).

*Longitudinal section form.*—Nearly round.

*Transverse section through diameter.*—Round.

*Suture.*—Shallow and inconspicuous except for a crease on the stem end of the fruit.

*Ventral surface.*—Usually rounded.

*Base.*—Slightly cordate.

*Apex.*—Usually rounded to slightly obtuse.

*Crater at stem attachment.*—Flaring circular with slight suture crease at the stem end; depth is 9 to 10 mm; breadth is 15 mm at top and 5 mm at pedicel attachment.

*Skin.*—Thickness: Medium in comparison to commercial peach varieties. Texture: Medium in comparison to standard varieties. Tenacity: Tenacious to flesh. Color: Red, American Beauty (Pantone 19-1759), over 70 to 90% of skin; ground color is cream, Dawn (Pantone 12-0811); fruit exposed to sunlight have a higher degree of enhanced red skin. Tendency to crack: None observed. Taste: No astringency observed. Epidermis: Pubescent, but visually shorter than 'UFSharp'.

*Flesh.*—Ripens: Evenly within each fruit. Texture: Firm, but juicy and non-melting when fully ripe. Fibers: Very fine, small, tender, and abundant. Aroma: Moderate and in the middle range of commercial peach varieties. Eating quality: Good, moderately sweet, slightly acid; soluble solids average 12.5 to 14 brix at 3.2 to 2.4 kg penetrometer firmness with a standard 5/16 inch tip. Juice: Abundant. Color: Cream, Vanilla (Pantone 12-0712), with no red in the flesh or at the pit. Browning by oxidation: Moderate on cut fruit when tree ripe and beginning to soften. Amygdalin: Undetected. Texture: Smooth, and similar to 'UFSharp'.

*Stone.*—Type: Clingstone. Size: Medium small: average length is 28 mm; average width is 25 mm; average thickness is 18 mm; average wall thickness is 5 mm. Color: Light Brown, Buckskin (Pantone 16-1342) when flesh is freshly cut.

*Form.*—Slightly oblong. Base: Straight. Apex: Rounded. Sides: Near equal. Surface: Irregularly shallow furrowed. Ridges: Shallow and rounded. Tendency to split: None observed.

*Seed.*—Bitter (amygdalin is abundant) kernel; viable if stratified upon removal from fruit at harvest, and cultured on a germination medium; kernel is brown, Gold Earth (Pantone 15-1234) when first removed from ripe fruit; seed is 28 mm length, 18 mm wide and 4 mm thick; shape is acute tip with obtuse base and overall ovate shape.

*Use.*—Fresh; dessert.

*Keeping quality.*—Excellent after 10 days at 2C and with minimal bruises or scarring appearing on skin.

*Shipping quality.*—Degree of firmness at harvest and firmness retained in refrigeration for 10 days at 2C, with no internal breakdown of flesh or appreciable loss of eating quality, indicates fruit should be highly acceptable for shipping.

Resistance to insects, disease or pests: High resistance to bacterial spot incited by *Xanthomonas campestris* pv. *pruni* (Pers.) Diet; resistance to other fruit and tree diseases are within the range for commercial peach cultivars in Florida; no unusual resistance or susceptibility to insects and diseases noted.

We claim:

1. A new and distinct cultivar of peach tree as shown and described herein.

* * * * *